(12) United States Patent
Elliott

(10) Patent No.: US 6,417,761 B1
(45) Date of Patent: Jul. 9, 2002

(54) STORAGE CASE FOR AN ORTHODONTIC RETAINER AND THE LIKE

(76) Inventor: Mary Margaret Elliott, 3910 Indian Way, Santa Ynez, CA (US) 93460

( * ) Notice: Subject to any disclaimer, the term of this patent is extended or adjusted under 35 U.S.C. 154(b) by 0 days.

(21) Appl. No.: 09/833,184

(22) Filed: Apr. 10, 2001

(51) Int. Cl.[7] .................................................. G08B 1/00
(52) U.S. Cl. ............................ 340/309.15; 340/568.1; 128/859; 128/861; 200/85 R; 206/63.5; 368/244
(58) Field of Search ................... 340/309.15; 200/85 R, 200/61.2; 206/83, 63.5, 6.1; 128/859, 861; 368/150, 151, 139, 255, 244, 250, 249, 276; 433/229, 216

(56) References Cited

U.S. PATENT DOCUMENTS

| | | | | |
|---|---|---|---|---|
| 4,094,326 A | * | 6/1978 | Newman | 131/234 |
| 4,615,681 A | * | 10/1986 | Schwarz | 434/236 |
| 4,934,534 A | * | 6/1990 | Wagner | 206/568 |
| 5,020,037 A | * | 5/1991 | Raven | 368/10 |
| RE35,034 E | * | 9/1995 | Albert | 206/63.5 |
| 5,915,558 A | * | 6/1999 | Girvetz | 206/534 |
| 6,301,196 B1 | * | 10/2001 | Daniel | 368/10 |

* cited by examiner

Primary Examiner—Jeffery Hofsass
Assistant Examiner—Davetta W. Goins
(74) Attorney, Agent, or Firm—Michael G. Petit

(57) ABSTRACT

A portable case for storing an orthodontic retainer. The case includes a movable cover that provides access to the interior of the case. A switch mounted within the case actuates a timer circuit when the retainer is disposed within the case and the cover of the case is closed. After the retainer is placed within the container and the cover is closed, the timer begins counting. When a preset period of time has elapsed, the timer actuates an audible signal generator. Upon actuation, the audible signal generator generates a pulsed audible signal such as a beep. The audible signal is preferably generated periodically, with progressively shorter intervals between audible signal pulses. The audible pulses serve to remind the owner to replace the retainer in his or her mouth after eating. Further, in the event that the case is misplaced, the audible signal can be used to locate the retainer case.

4 Claims, 3 Drawing Sheets

FIG. 6 shows an illustrative train of audible signal pulses generated by the audible signal generator as a function of time after initiation of the timer when the cover of the container housing a retainer is closed.

STORAGE CASE FOR AN ORTHODONTIC RETAINER AND THE LIKE

BACKGROUND OF THE INVENTION

1. Field of the Invention

A container for storing articles, and more particularly, a case for storing an orthodontic retainer that provides an audible signal when the retainer is closed within the case.

2. Prior Art

An orthodontic retainer is a device used for straightening teeth. In order for orthodontic retainers to perform their intended function, they must be consistently worn in the mouth until the teeth are correctly positioned and preferably until the tooth root system becomes firm within the supporting bone structure. While children may remove the retainer for eating or brushing the teeth, it is advantageous that the retainer be replaced within the mouth as soon as is practicable thereafter. Accordingly, for sanitary purposes, most retainers are dispensed with a case for storing the fixture while it is out of the mouth.

People who have children with orthodontic retainers recognize the problem of enforcing consistent use of the retainer. While children may use the case for the temporary storage of the retainer during activities requiring removal from the mouth but frequently forget to replace the retainer within the mouth as instructed when such activity is terminated. It is desirable to provide a case for temporarily storing an orthodontic retainer that signals the owner to remove the retainer from the case for reinsertion within the mouth after a reasonable period of storage time has elapsed.

SUMMARY

It is a first object of the invention to provide a case for the temporary and sanitary storage of an orthodontic retainer fixture.

It is a further object of the invention to provide a case for the temporary and sanitary storage of an orthodontic retainer fixture wherein the case provides an audible signal when the retainer has been disposed within the case for a predetermined period of time.

The features of the invention believed to be novel are set forth with particularity in the appended claims. However the invention itself, both as to organization and method of operation, together with further objects and advantages thereof may be best understood by reference to the following description taken in conjunction with the accompanying drawings in which:

DESCRIPTION OF THE PREFERRED EMBODIMENTS

Figure 1:
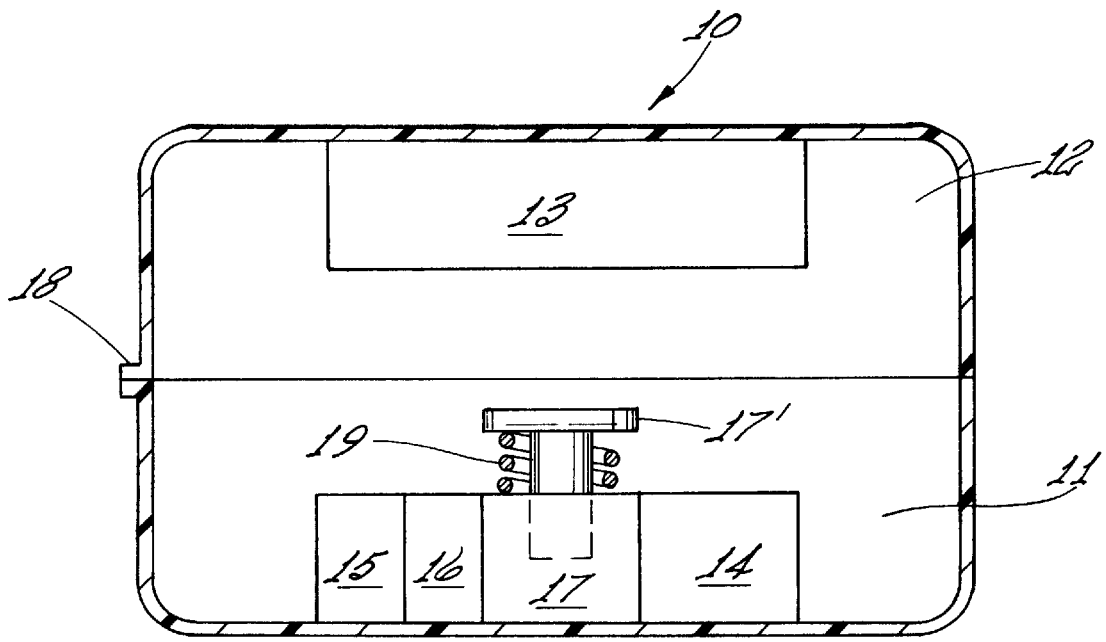
FIG. 1 is a partially cross-sectional side view of a retainer case in accordance with the present invention with the retainer removed and the case closed.
Figure 2:
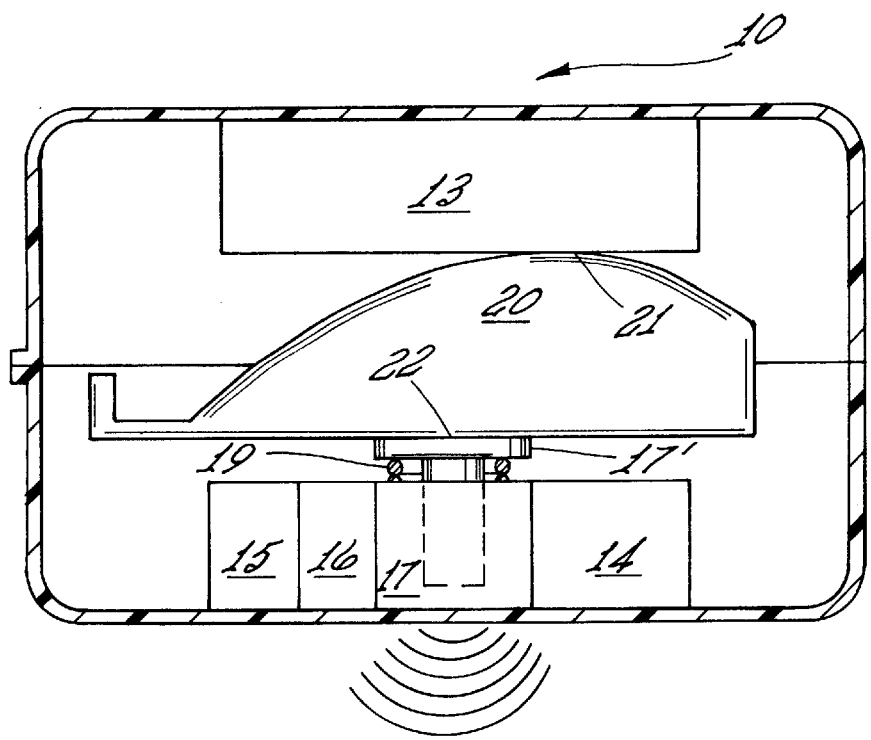
FIG. 2 is a partially cross-sectional side view of a retainer case in accordance with FIG. 1 wherein a retainer is disposed within the case and the case cover is closed.
Figure 3:
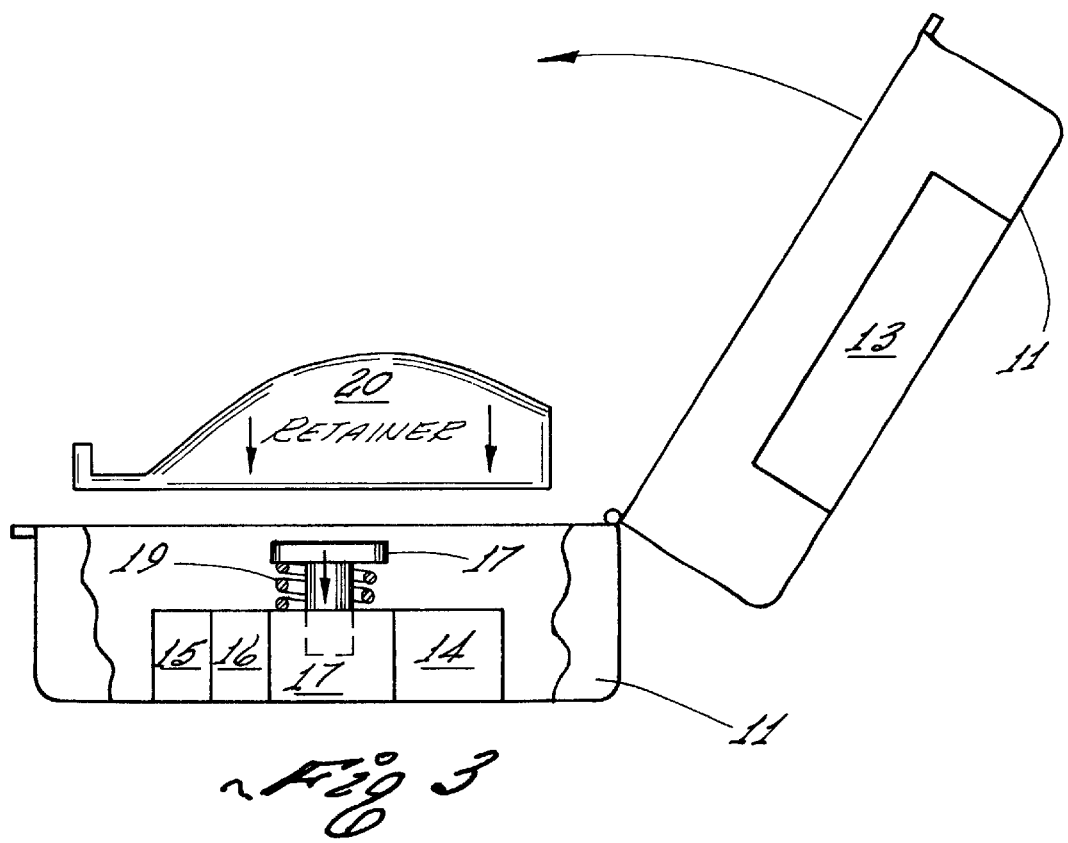
FIG. 3 is a partially cutaway side view of a retainer case in accordance with FIGS. 1 and 2 illustrating the relative relationship between the case bottom, case cover, a retainer and the switch comprising the case with the case cover open in preparation for storing the retainer.

Turning now to FIG. 1, an orthodontic retainer case in accordance with the present invention is indicated at numeral 10. The case 10 has a bottom 11 and a hinged cover 12. The cover 12 has a foam pad 13 affixed to the lower (inner) surface thereof. An audible signal generating device 14, a DC power source 15 such as a battery, and a resettable timer 16 are affixed to the bottom 11 of the case 10. Alternatively, the cover 12 may be attached to the bottom 11 by any attachment means, such as mating threads or a snap fit, that provide a snug fitting between the cover and the bottom when the cover is closed as shown in FIGS. 1 and 2. A pressure actuated on/off switch 17 having a spring-loaded switch actuator 17' is attached to the bottom of the case and positioned therewithin such that when a retainer is placed in the bottom, in the manner illustrated in FIG. 2, and the cover closed, the switch actuator 17' is depressed thereby setting the switch 17 in the "on" position. When the case is open or the retainer removed, a spring 19 urges the switch actuator 17' upwardly thereby setting the switch 17 in an "off" condition. The case 10 may further include a latch 18 operable for releasably engaging the cover and the bottom.

When an orthodontic retainer 20 is placed within the bottom 11 of the case 10, as shown in FIG. 2, and the cover 12 closed as shown, the elastically compressible foam pad 13 urges the retainer 20 downwardly against the switch actuator. The pressure compresses spring 19, depressing the switch actuator 17' and turning switch 17 "on" which, in turn, actuates the timer 16. Upon actuation, the timer 16 initiates counting and switches power from power source 15 to the audible signal generator 14 after a predetermined delay period T1 (FIG. 6) has elapsed. The delay period T1 is determined such that the owner of the retainer (hereinafter, the "user") can reasonably complete a task requiring removal of the retainer from the mouth such as eating or tooth brushing before the audible alarm sounds. The timer 16 is set such that the delay period T1 is appropriate to the user's activity. For example, when the retainer is placed in the case while eating, the delay period T1 is preferably about 10–30 minutes. When the delay period T1 has elapsed, a pulsed audible signal is generated having a duration of about 1 second. If the cover of the case is not opened within a period of time ΔT(t) after generation of the initial audible signal pulse, a second pulse is generated. The process is repeated with the time between subsequent pulses ΔT(t) decreasing until the cover is raised to place the switch 17 in an "off" condition . When switch 17 is placed in the "off" position, the timer resets the clock for counting delay time. The switch 17 is placed in the "off" position and the audible signal generator 14 is disabled by either removing the retainer 20 from the case 10 or by merely opening the cover 12.

Figure 4:
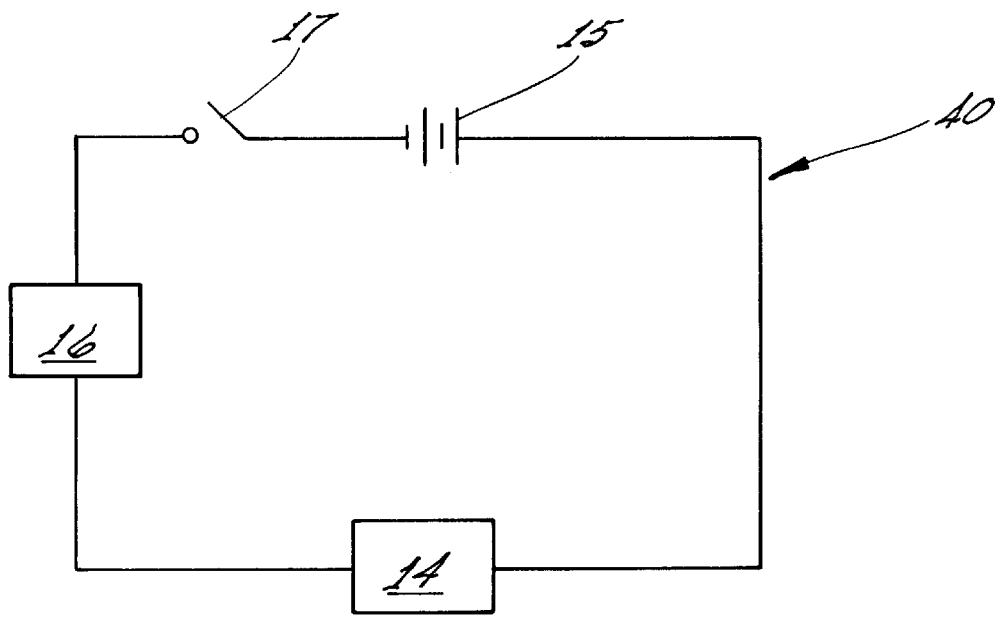
FIG. 4 is a schematic diagram of an embodiment of a switch-actuated electrical circuit suitable for use in a retainer case in accordance with the present invention.
Figure 6:
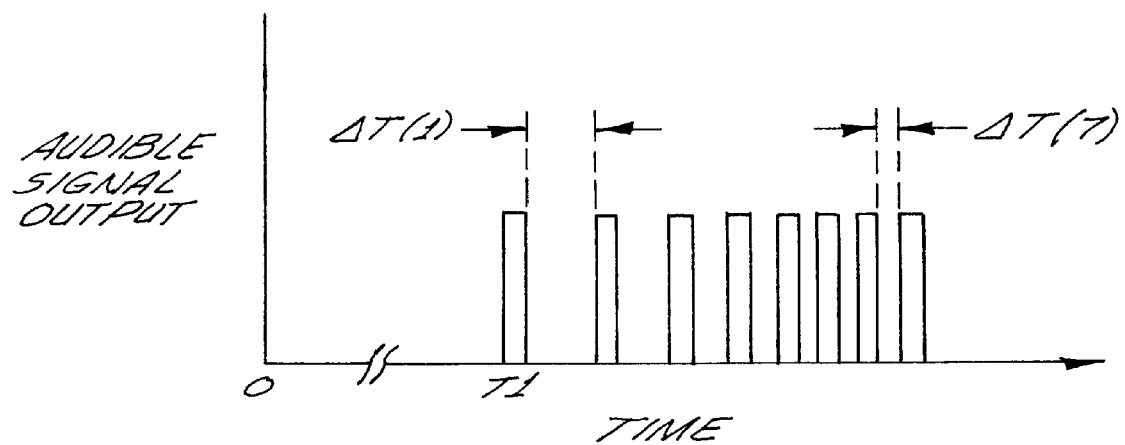

An exemplary audio signal generating circuit is presented in FIG. 4. The circuit has the following essential components: a power source 15 for energizing the curcuit 40, which is preferably a DC electrical power source such as a battery; a switch 17 for turning the circuit on and off; a timer 16, which may be analog or digital; and an audible signal generator 14. The audible signal generator 14 preferably comprises a piezo driver which receives its input power from the power source 15 under control of the timer and supplies a train of AC voltage pulses to a piezoelectric transducer device. The piezo driver preferably supplies power to the piezoelectric transducer device in a frequency range of 4–7 kHz in 1 second pulses spaced a time interval ΔT(t) apart. The time interval between pulses ΔT(t) preferably decreases as time increases, with an initial maximum interval ΔT(1) of preferably about 30–120 seconds and a minimum time interval ΔT(7) of 1 second or less after an appreciable period of time has elapsed following T1. The decrease in the time interval between pulses serves to increasingly focus the user's attention to the event. A representative train of audible pulses emanating from the audible signal generator is illustrated in FIG. 6.

A piezoelectric transducer device suitable for the present application is a monomorphic element such as is currently used in audible signalling devices such as pagers which employ an essentially single tone alert signal. A suitable piezoelectric transducer for the present application is a ceramic disk bonded to a metallic backplate. The monomorphic piezoelectric element resonates at a predetermined frequency when excited with electrical energy and exhibits a frequency response curve centered about a predetermined resonant frequency within the audible spectrum. An essentially single tone acoustic signal is generated by such a monomorphic element with a frequency response dropping off rapidly on either side of the resonant frequency of the piezoelectric transducer.

A case adapted for storing an orthodontic retainer constructed in accordance with the invention includes a piezoelectric element acoustically coupled to the inside surface of the bottom 11 of the case 10. The piezoelectric transducer device is used as a buzzer and is driven by a driver which supplies a driving frequency of about 4–7 kHz. The case bottom 11 may be used as the vibration plate of the buzzer and is preferably formed so that the resonance frequency thereof is between 4 kHz and 7 kHz.

Figure 5:
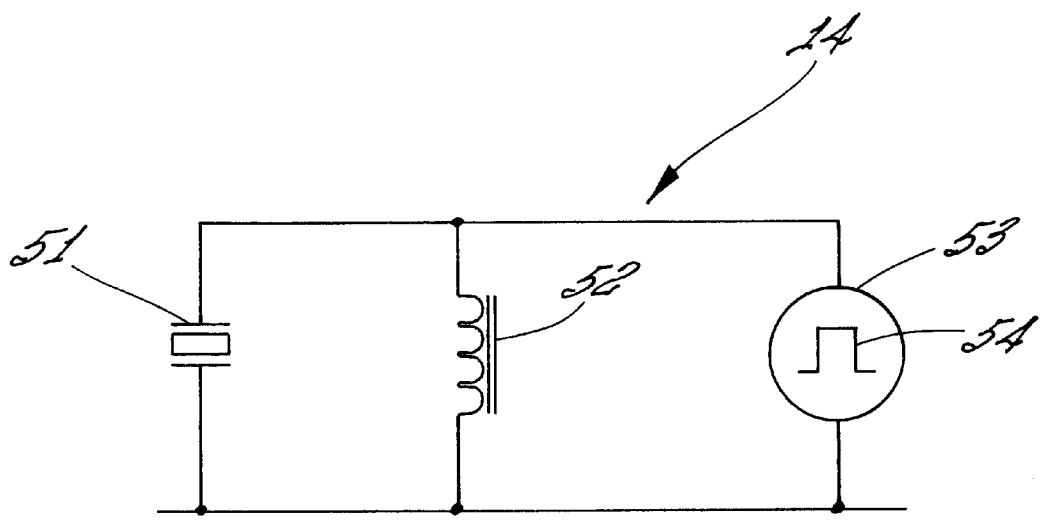
FIG. 5 is a schematic diagram of an audible signal generator showing a driving circuit for a piezoelectric transducer device conformed to be used as an alert buzzer.

With reference now to FIG. 5, an audible signal generator 14 comprising a piezoelectric transducer and a driving circuit suitable for energizing the piezoelectric transducer is illustrated. Piezoelectric element 51 is coupled in parallel to a transformer 52 which, in turn, is connected in parallel to a driver 53 which supplies a driving pulse wave 54. Pulse wave 54 is applied across transformer 52 and drives piezoelectric element 51. The audible sound signal is emitted from piezoelectric element 51 by applying the self-induced voltage of transformer 52 thereto which generates an audible signal.

In summary, a storage case for an orthodontic retainer is provided that produces an audible signal alerting the user that the retainer is in the storage case and, therefore, not in use, and providing a reminder to the user to replace the retainer in the mouth. The audible signal is only generated when the retainer is in the case and the case is closed. Accordingly, the audible signal may be used as a beacon to direct the user to the case in the event the case is misplaced. The event that triggers the audible signal generation is the placement of a retainer within the case and closing and latching the case cover to seal the retainer within the case.

The thickness of the foam pad 13 may be varied to adjust to the thickness of the retainer or similar article to assure that the switch is activated (i.e., "on") when the article is in the case and the cover closed. The aforesaid event actuates a timer that initiates a countdown defining a predetermined delay period T1. When the delay period has elapsed, a piezoelectric transducer driver is energized. The piezoelectric transducer driver supplies pulsed energy having a predetermined pulse width and duty cycle to the piezoelectric transducer device. The audible signal produced by the piezoelectric transducer continues with increasing regularity until the cover of the case is opened.

While particular embodiments of the present invention have been illustrated and described, it would be obvious to those skilled in the art that various other changes and modifications can be made without departing from the spirit and scope of the invention. For example, the case may be used for storage of articles similar to a orthodontic retainer wherein periodic storage of the article is required during the performance of a task. It is therefore intended to cover in the appended claims all such changes and modifications that are within the scope of this invention.

What I claim is:

1. A storage case for an orthodontic retainer operable for providing an audible signal when a retainer is sealed within the case for a predetermined period of time comprising:
    (a) a container having a bottom portion and a cover attached thereto, said cover adapted to be lockingly engaged to said bottom portion, said cover having an inner bottom-facing surface and said bottom portion having an inner cover-facing surface, said container having an interior volume dimensioned to receive an orthodontic retainer therewithin;
    (b) a foam pad affixed to said inner bottom-facing surface of said cover;
    (c) a source of electric power;
    (d) an audible signal generator affixed to said inner cover-facing surface of said bottom portion;
    (e) a timer operable for switching power from said source of electrical power to said audible signal generator when said timer is actuated; and
    (f) a switch disposed within said container, said switch being operable for actuating said timer when a retainer is placed within said container and said cover locked in sealing engagement with said bottom portion.

2. A storage case for an orthodontic retainer in accordance with claim 1 wherein said audible signal generator comprises a piezoelectric transducer and a piezoelectric transducer driver.

3. A storage case for an orthodontic retainer in accordance with claim 2 wherein said piezoelectric transducer driver provides a periodic audio frequency electrical voltage signal to said piezoelectric transducer when said timer is actuated.

4. A storage case for an orthodontic retainer in accordance with claim 2 wherein said audible signal generator is operable for providing a plurality of audible pulses.

* * * * *